US011256106B2

(12) United States Patent
Peterson (10) Patent No.: US 11,256,106 B2
(45) Date of Patent: Feb. 22, 2022

(54) LED ILLUMINATION SYSTEM

(71) Applicant: Medical Instrument Development Laboratories, Inc., San Leandro, CA (US)

(72) Inventor: Erik W. Peterson, Walnut Creek, CA (US)

(73) Assignee: MEDICAL INSTRUMENT DEVELOPMENT LABORATORIES, INC., San Leandro, CA (US)

(*) Notice: Subject to any disclaimer, the term of this patent is extended or adjusted under 35 U.S.C. 154(b) by 287 days.

(21) Appl. No.: 16/672,022

(22) Filed: Nov. 1, 2019

(65) Prior Publication Data

US 2020/0142206 A1  May 7, 2020

Related U.S. Application Data

(60) Provisional application No. 62/754,380, filed on Nov. 1, 2018.

(51) Int. Cl.
*G02B 27/14* (2006.01)
*G02B 27/30* (2006.01)
*G02B 6/35* (2006.01)
*G02B 6/12* (2006.01)

(52) U.S. Cl.
CPC ......... *G02B 27/141* (2013.01); *G02B 6/3564* (2013.01); *G02B 27/30* (2013.01); *G02B 2006/12104* (2013.01)

(58) Field of Classification Search
CPC ...... A61F 9/00736; G02B 2006/12104; G02B 21/0012; G02B 21/06; G02B 26/02; G02B 27/1006; G02B 27/141; G02B 27/30; G02B 6/29361; G02B 6/29395; G02B 6/3564; G02B 6/4214; G02B 6/4215
See application file for complete search history.

(56) References Cited

U.S. PATENT DOCUMENTS

| 6,532,316 B1 | 3/2003 | Cao |
| 7,076,146 B2 | 7/2006 | Sufleta et al. |
| 7,189,226 B2 | 3/2007 | Auld et al. |
| (Continued) | | |

FOREIGN PATENT DOCUMENTS

WO    2012/090520 A1    7/2012

OTHER PUBLICATIONS

International Search Report and Written Opinion for Application No. PCT/US2019/059373 dated Jan. 27, 2020 (16 pages).

*Primary Examiner* — Joseph P Martinez
*Assistant Examiner* — Vipin Patel
(74) *Attorney, Agent, or Firm* — Michael Best & Friedrich LLP (57) ABSTRACT

An optical system for adjusting a proportion of light of a particular spectral band that is emitted from the optical system. A dichroic mirror is configured to reflect light of a first spectral band from a light source towards a distal end of an optical fiber while allowing light of a second spectral band to pass through the dichroic mirror. The second mirror is positioned behind the dichroic mirror and is configured to reflect light of the second spectral band. A mirror actuator is coupled to the second mirror and is configured to adjust a proportion of the light of the second spectral band that is emitted by the optical system by adjusting a position of the second mirror relative to the dichroic mirror.

6 Claims, 9 Drawing Sheets

(56) References Cited

U.S. PATENT DOCUMENTS

| | | | |
|---|---|---|---|
| 7,307,774 B1 * | 12/2007 | Schnitzer | G01N 21/6458 359/198.1 |
| 8,688,401 B2 | 4/2014 | Papac et al. | |
| 8,992,021 B2 | 3/2015 | Smith | |
| 2002/0087149 A1 | 7/2002 | McCary | |
| 2011/0144745 A1 | 6/2011 | Martin et al. | |
| 2019/0209372 A1 | 7/2019 | Farley | |

* cited by examiner

LED ILLUMINATION SYSTEM

RELATED APPLICATIONS

This application claims the benefit of U.S. Provisional Patent Application No. 62/754,380, filed Nov. 1, 2018, entitled "LED ILLUMINATION SYSTEM," the entire contents of which are incorporated herein by reference.

BACKGROUND

The present invention relates to methods and systems for illumination with specific wavelengths of light.

SUMMARY

Vitreoretinal surgery is performed with visualization under a microscope and requires good illumination into the posterior chamber of the eye. Illumination from the exterior, coaxial with the optical path of the microscope, is possible but is not optimal because of reflections and scattering at the various structures in the anterior portion of the eye. Normal practice is to deliver light directly into the posterior chamber through a fiberoptic delivery system. Such fiberoptic devices are often referred to as endoilluminators.

The retina can be permanently damaged by exposure to intense light. Different portions of the light spectrum cause different types of damage. Light in the infrared portion of the spectrum can cause damage by thermal mechanisms. Light in the ultraviolet portion of the spectrum (which has a high photon energy) can break chemical bonds or otherwise stimulate chemical changes which damage the retina. This effect is often referred to as phototoxicity. Light in the blue portion of the visible spectrum also has sufficient photon energy to cause some phototoxicity.

Light sources for use with endoilluminators for vitreoretinal surgery have generally included filters to reduce ultraviolet and infrared emissions which may be produced by certain types of light source. With increasing awareness of blue light phototoxicity, it has become common to also provide a filter to reduce blue emission. The resulting illumination appears to be yellow. Surgeons sometimes experience difficulty with visualization under this yellow light, so the blue filter is typically removable. The surgeon can select white light when optimal visualization is required and select yellow light when reduction of phototoxicity is more important.

In one embodiment, the invention provides an optical system including a light source, a dichroic mirror, and a second mirror. The dichroic mirror is configured to reflect light of a first spectral band from the light source towards a distal end of an optical fiber while allowing light of a second spectral band to pass through the dichroic mirror. The second mirror is positioned behind the dichroic mirror and is configured to reflect light of the second spectral band. A mirror actuator is coupled to the second mirror and is configured to adjust a proportion of the light of the second spectral band that is emitted by the optical system by adjusting a position of the second mirror relative to the dichroic mirror. Adjusting the position of the second mirror relative to the dichroic mirror alters the amount of the light of the second spectral band that is reflected by the second mirror towards the distal end of the optical fiber.

In some embodiments, the light source includes a "white" LED that emits light including blue light. In some embodiments, the dichroic mirror is short-pass dichroic mirror, which transmits light of shorter wavelengths (including the blue light) and reflects light of longer wavelengths. In some embodiments, the blue light that passes through the dichroic mirror is reflected by the second mirror and, by adjusting the position of the second mirror relative to the dichroic mirror, the system is able to controllably adjust a proportion of blue light that is included in the light that is emitted from the optical system.

In some embodiments, the position of the second mirror is adjusted relative to the dichroic mirror by rotating the second mirror and, in other embodiments, the position is adjusted by linear movement of the second mirror.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 1:
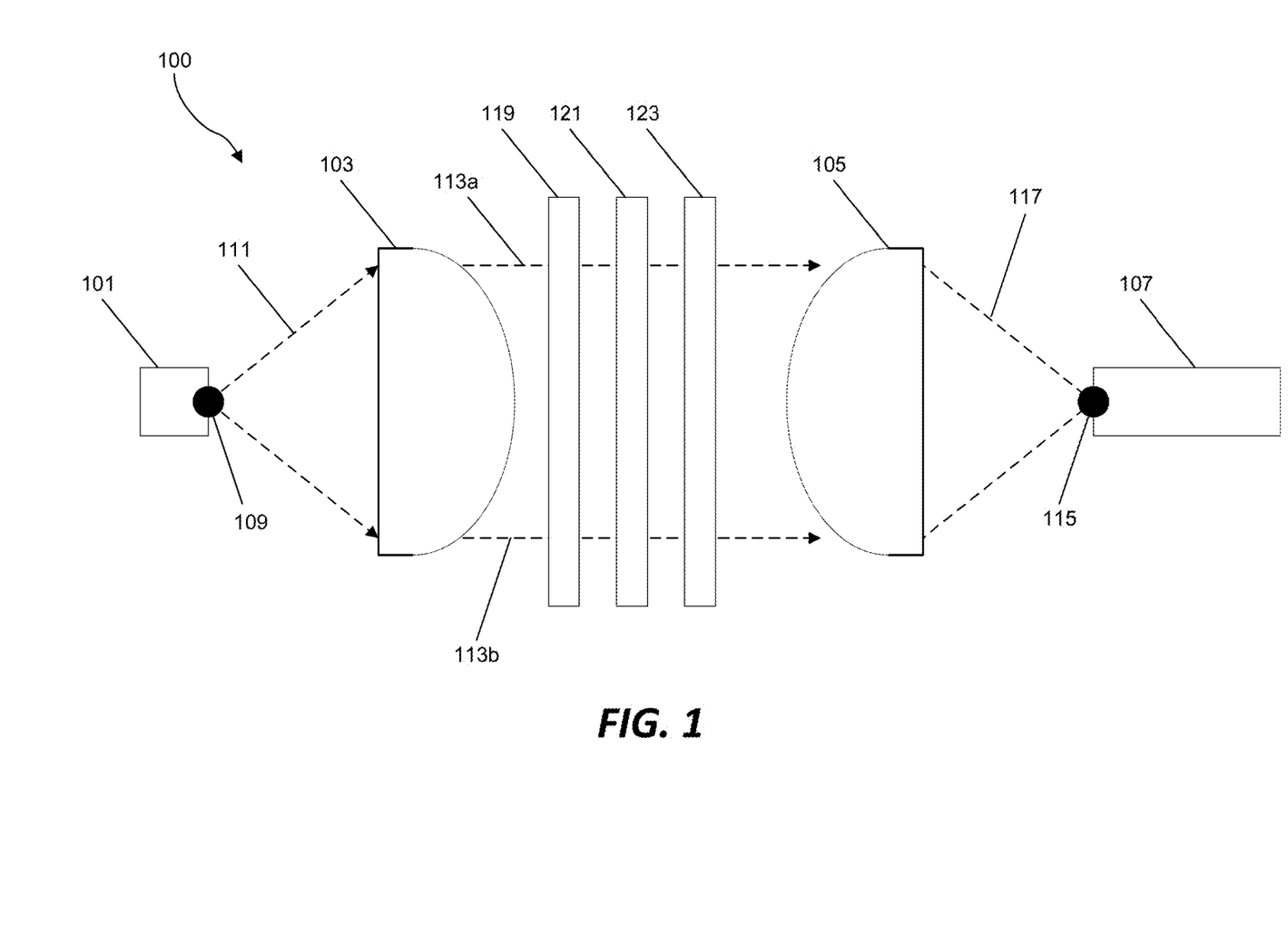
FIG. 1 is a schematic diagram of an illumination system with optical elements positioned in a generally linear optical path.

FIG. 1 illustrates an optical system 100 for coupling a source of light 101 to the input end of an optical fiber 107. The source of light emission 101 is positioned at or near the focal point 109 of a first lens 103. Light rays 111 from the light source 101 enter the first lens 103 are collimated (made parallel to each other) in the region between the first lens 103 and a second lens 105. The collimated light beam in the region between the first lens 103 and the second lens 105 are illustrated in the example of FIG. 1 by parallel lines labelled 113a and 113b. Parallel rays entering the second lens 105 are focused by the second lens 105 toward a focal point 115 of the second lens 105. The input end of the optical fiber 107 is located at or near the focal point 115 of the second lens 105 so that the focused light 117 from the second lens 105 enters the optical fiber 107.

In practice, the light source 101 is not a single point, but emits light from a surface or volume with finite dimensions. In the optical system illustrated, a real image of this light-emitting area is projected at or near the focal point 115 of second lens 105. To achieve optimal coupling of light into optical fiber 107, the end of the optical fiber 107 is placed at or near the location of this image, i.e. near the focal point 115 of the second lens 105.

One advantage of this optical system is that the properties of the light entering the fiber 107 can be modified by arranging various optical elements in the optical path of the collimated beam between the first lens 103 and the second lens 105. In some implementations, these optical elements can include one or more filters to modify the spectrum of the light. In various implementations, the system may be configured to include one or more fixed filters and mechanisms for one or more selectively removable (or interchangeable) filters. In the specific example of FIG. 1, the optical elements positioned in the optical path between the first lens 103 and the second lens 105 include a first fixed filter 119 to remove infrared light, a second fixed filter 121 to remove ultraviolet light, and a removable filter 123 to selectively remove blue light. This specific combination of filters may be selected to reduce the potential for damage to the retina caused by harmful light wavelengths. In some implementations, the optical elements positioned in the optical path between the first lens 103 and the second lens 105 may include other types of optical elements in addition to or instead of optical filters. For example, in some implementations, an attenuating mechanism, such as an iris, may be positioned in the optical path between the first lens 103 and the second lens 105 to controllably modify the intensity of the light coupled to the fiber 107.

Optical filter (such as, for example, those discussed above in reference to FIG. 1) may be configured/designed to selectively transmit only a portion of the spectrum of light. It is also possible to construct optical elements that selectively reflect only a portion of the spectrum. For example, a dichroic (two color) mirror reflects light in one portion of the spectrum and transmits light in a different portion of the spectrum. An example found in some optical systems, such as slide projectors, is the so-called "cold mirror". A cold mirror reflects light in the visible portion of the spectrum and transmits the infrared portion of the spectrum, thereby removing it from the reflected beam.

Figure 2:
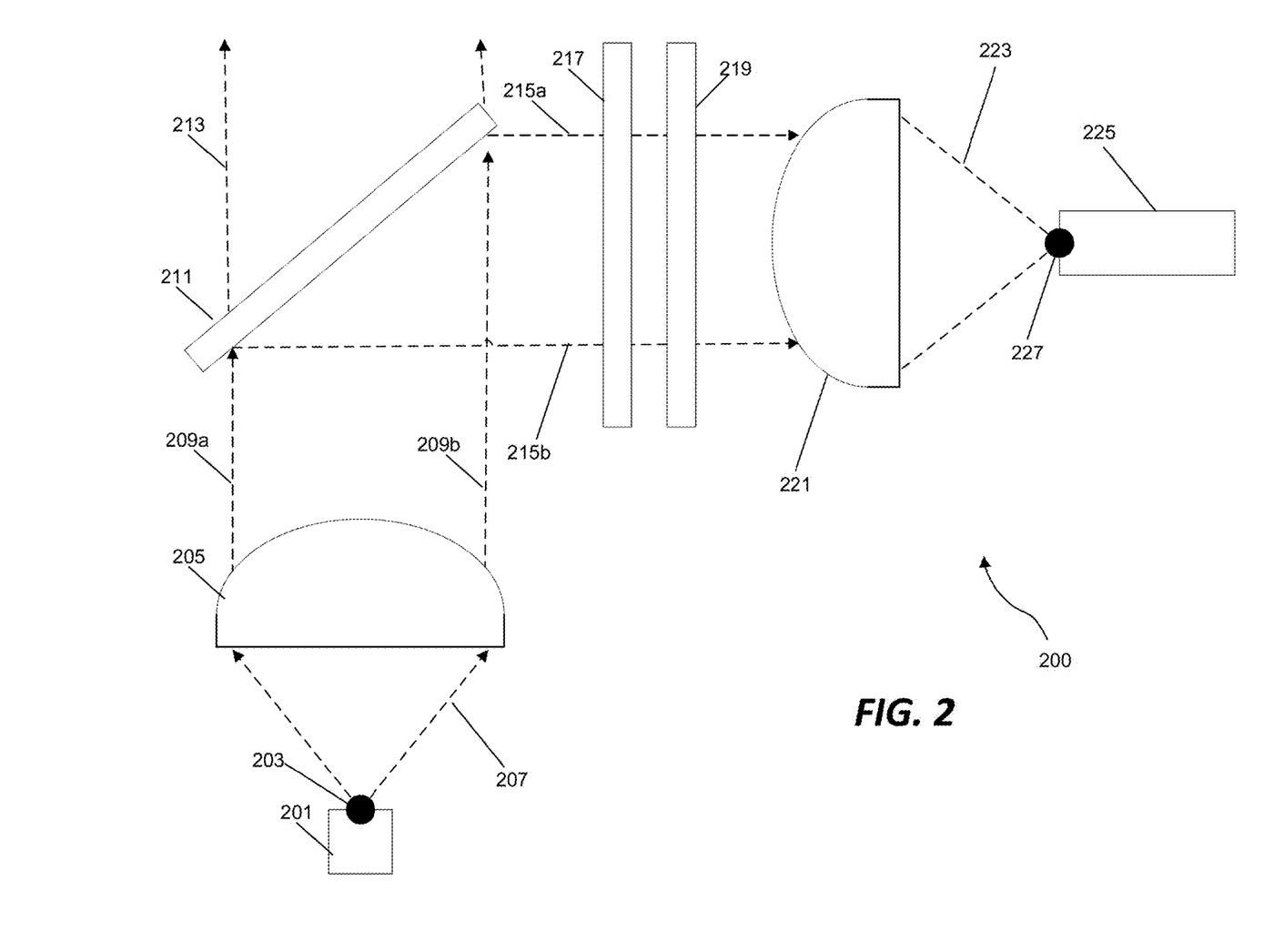
FIG. 2 is a schematic diagram of an illumination system with a "cold" mirror configured to selectively reflect light of a particular wavelength (or bandwidth of wavelengths) along an angled optical path from a light source to an input end of an optical fiber.

FIG. 2 illustrates an example of another optical system 200 in which a cold mirror 211 is used to remove infrared energy instead of a spectral filter. A light source 201 positioned near the focal point 203 of a first lens 205 projects light 207 that is collimated (i.e., collimated beam illustrated by lines 209a and 209b) by the first lens 205 and directed toward the cold mirror 211. Any infrared light in the collimated beam 209a, 209b (i.e., light of wavelengths in the infrared spectral band) passes through the cold mirror 211 (as illustrated by collimated beam 213) and is removed from the optical path. However, light from the collimated beam 209a, 209b that is within the visible light spectral band is reflected by the mirror 211 (as illustrated by collimated beam 215a, 215b) and redirected along an angled optical path through a first filter 217 and a second filter 219 to a second lens 221. The second lens 221 focuses the light 223 towards an input end of an optical fiber 225 positioned at or near the focal point 227 of the second lens 221.

The source of light used in these examples can take many different forms, including incandescent and arc lamps. In some implementations, the light source includes a "white LED" (light-emitting diode). However, the phrase "white LED" can be a bit of a misnomer, since the diode, in some implementations, does not emit "white" light. Instead, in some implementations, the diode is configured to emit light in the blue part of the spectrum and has a coating applied over the emitting surface. The coating contains phosphors that absorb some of the blue light and re-emit light at a longer wavelength, such as green or red wavelengths. With a suitable phosphor coating, the combined emissions from this type of LED can cover most of the visible spectrum (i.e., approximating "white" light).

Figure 3:
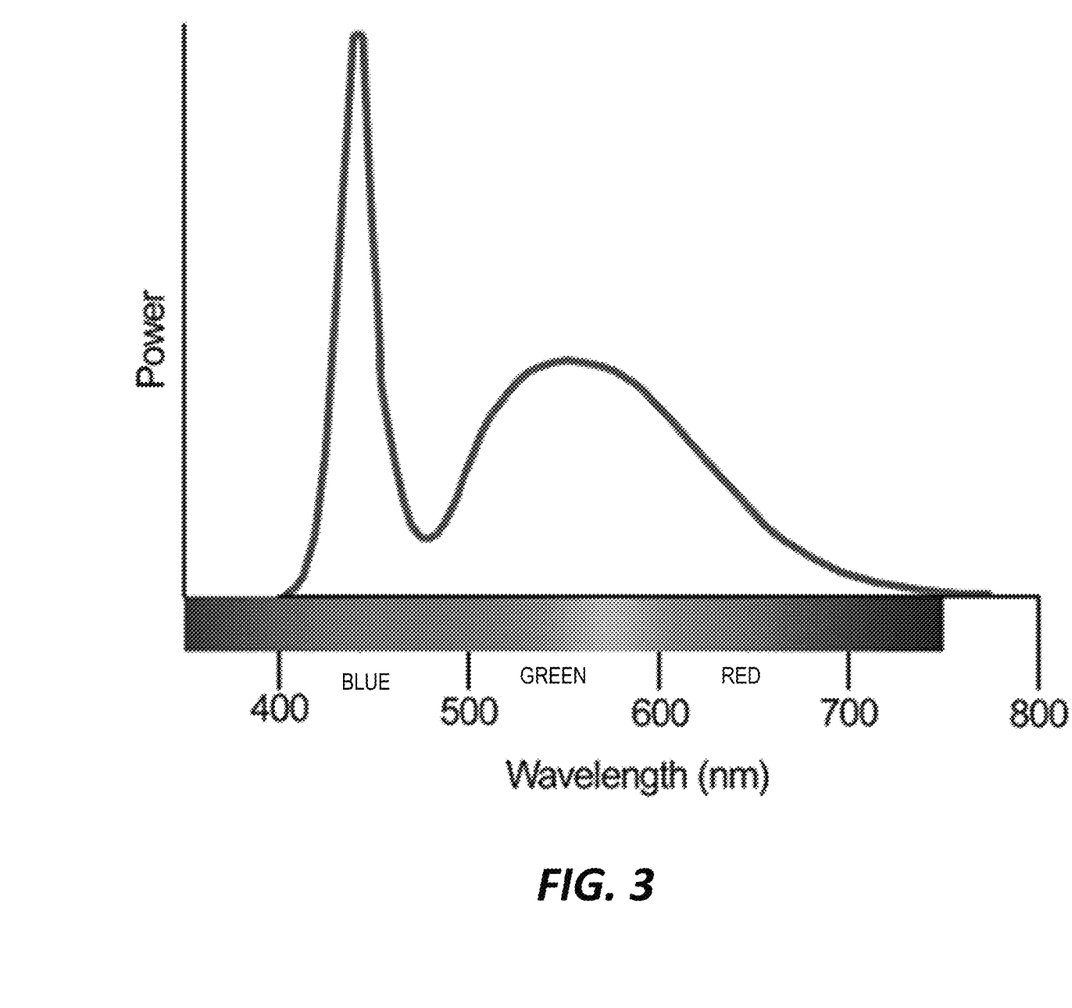
FIG. 3 is a graph of light spectrum emitted by an example of a "white" light emitting diode (LED).

FIG. 3 illustrates the spectrum of light emitted in an example of a "white" LED. This spectral distribution exhibits a peak in the blue portion of the spectrum, which is the direct emission from the diode, and the broadband distribution from green to red, resulting from the phosphor re-emission. Depending on the relative proportions of these two components, the perceived color can range from a "warm" yellowish white (low blue content) to a "cold" blueish white (high blue content). In some implementations, light from a "white LED" can provide a complete absence of ultraviolet emission. This is because no photons with a higher energy than the band gap of the diode itself can be emitted. "White LEDs" also typically include no more than negligible emission in the infrared portion of the spectrum. Consequently, optical filters might not be needed to protect the retina from these damaging wavelengths. Other advantageous features of the white LED include a very long operating life, high energy efficiency and a relatively low operating temperature.

The technology for white LEDs has been rapidly evolving, and some are now available which are suitable for fiberoptic illumination in vitreoretinal surgery. Because of their small size and relatively low operating temperature, coupling to the optical fiber can be as simple as placing the end of the fiber in contact with or adjacent to the emitting surface of the LED. However, this direct coupling does not provide any means for protecting the retina from blue light phototoxicity. In fact, as illustrated in FIG. 3, the white LED may have a peak of emissions in the blue part of the spectrum.

The examples illustrated below each include a mechanism to vary the proportion of blue light coupled between a white LED emitter and a fiberoptic delivery system. The user can adjust the output color from yellow (completely free of blue) through warm white to cold white, as appropriate for the task being performed. Although these examples are described below in specific reference to selectively adjusting a proportion of "blue light" that reaches the fiberoptic delivery system, the specific optical components may be adapted to control the proportional emission of other specific wavelengths or spectral bands of light.

Figure 4:
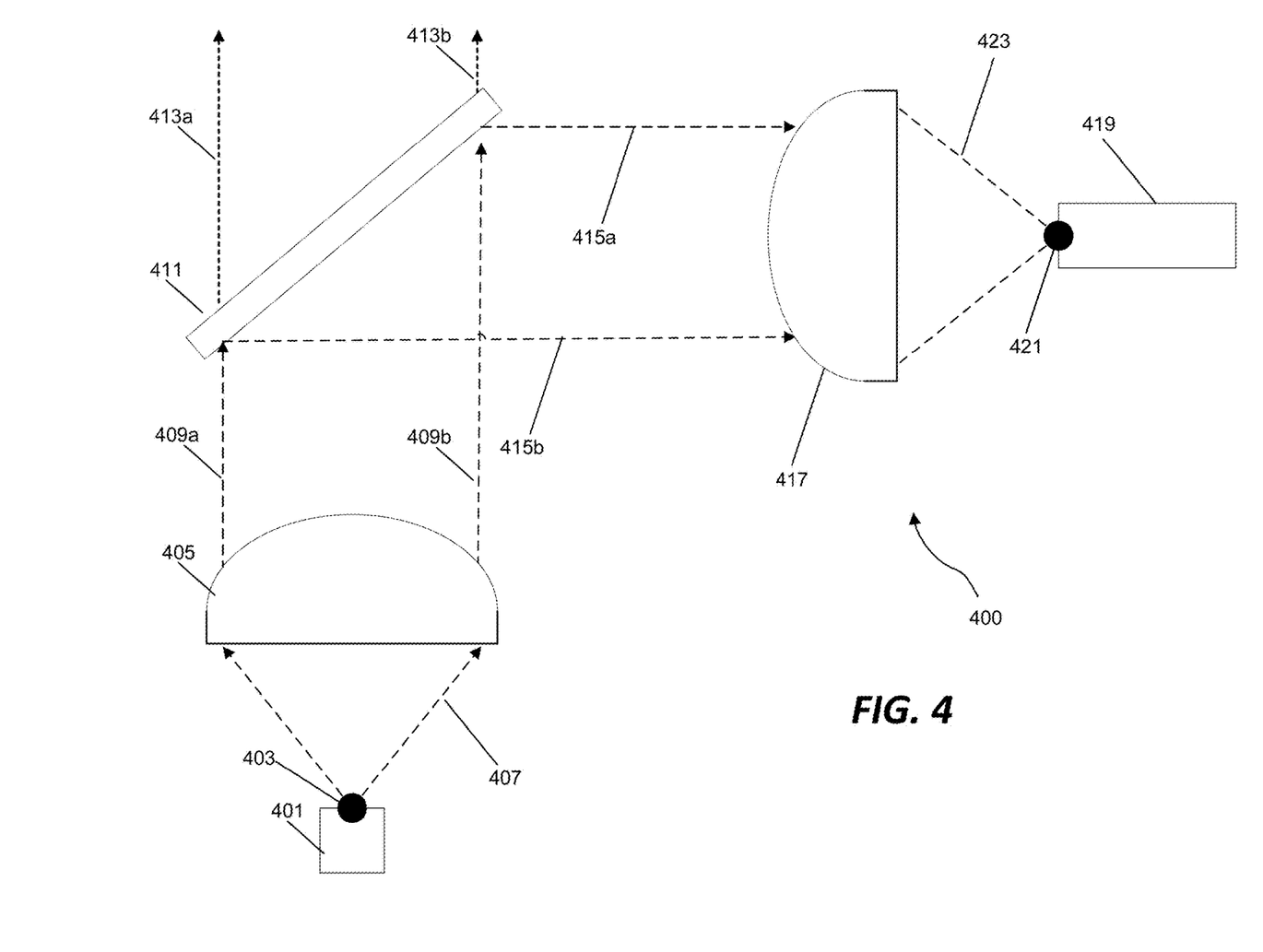
FIG. 4 is a schematic diagram of an illumination system with a dichroic mirror configured to selectively reflect light of a particular wavelength (or bandwidth of wavelengths) along an angled optical path from a light source to an input end of an optical fiber.

FIG. 4 illustrates an optical system 400 configured to produce a yellow (i.e., blue-free) output to an optical fiber. A white LED 401 positioned at or near the focal point 403 of a first lens 405 emits light 407 that is collimated by the first lens and projected as a collimated beam 409a, 409b to a mirror 411. The example of FIG. 2 above includes a "cold" mirror of a type known as a "long pass" mirror. It transmits long-wavelength infrared light and reflects shorter-wavelength visible light. In contrast, the mirror 411 in the example of FIG. 4 is a "short pass" dichroic mirror, which transmit shorter wavelengths (indicated by the collimated beam 413a, 413b) and reflect longer wavelengths (indicated by collimated beam 415a, 415b). Accordingly, the mirror 411 is configured with a cut-off wavelength such that blue light is transmitted (and thus removed from the reflected beam) (i.e., beam 413a, 413b) while longer wavelengths from green through red are reflected (i.e., beam 415a, 415b). The light reflected by the mirror 411 is redirected along an angled optical path towards a second lens 417 that focuses the light 423 toward the end of an optical fiber 419 positioned at or near the focal point 421 of the second lens 417.

Figure 5A:
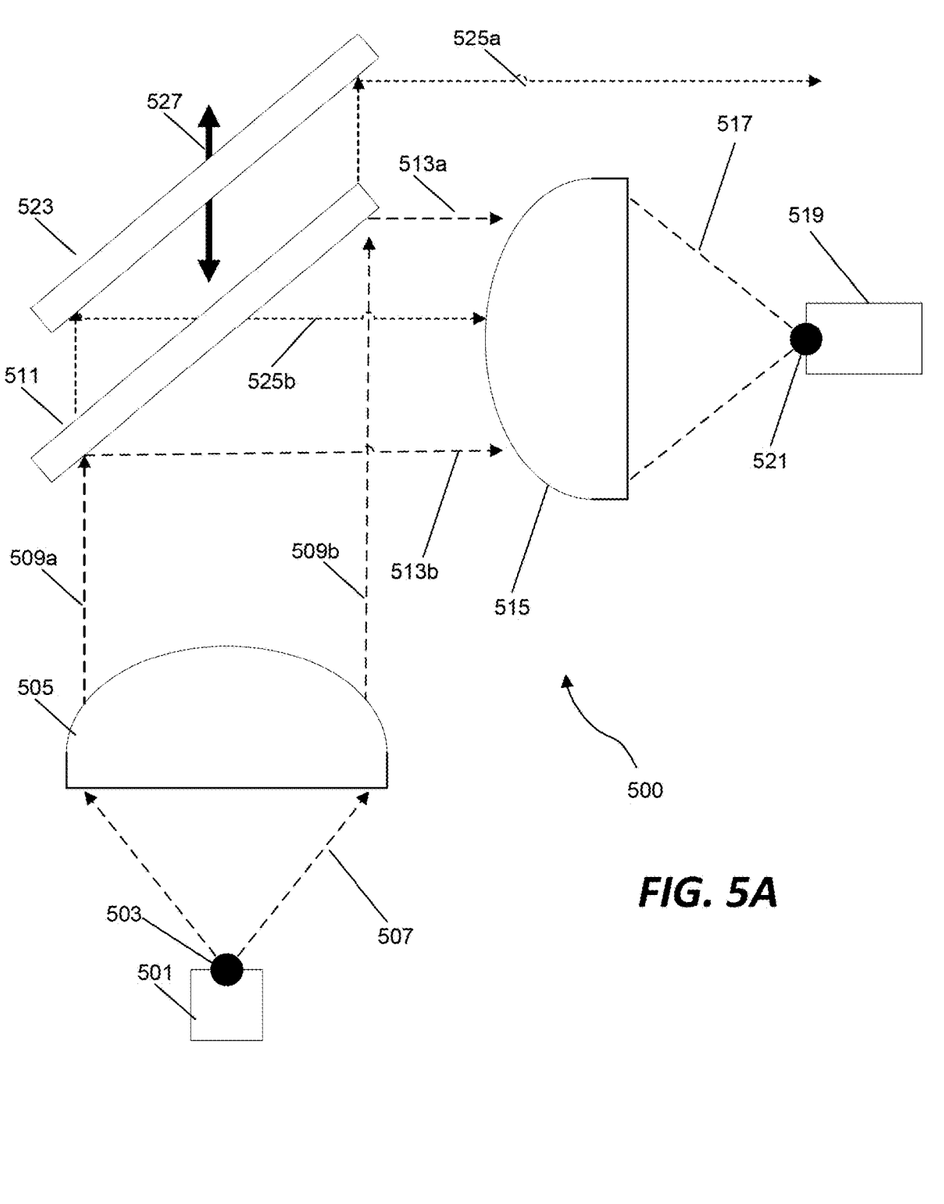
FIG. 5A is a schematic diagram of an illumination system configured to adjust an amount of light of a second spectral band that is projected to an input end of an optical fiber by controllably adjusting a linear position of a second mirror relative to a dichroic mirror.

FIG. 5A illustrates an example of another optical system 500 that utilizes a dichroic mirror 511 and a second mirror 523 to controllably adjust an amount of light of a particular spectral band that reaches the distal end of the optical fiber and is included in the light output of the optical system 500. A white LED 501 positioned at or near a focal point 503 of a first lens 505 emits light 507 that is collimated by the first lens 505. The collimated beam 509a, 509b is directed toward the dichroic mirror 511. Light in this collimated beam 509a, 509b that is of wavelengths in a first spectral band (or bands) is reflected by the dichroic mirror 511 toward a second lens 515 (as indicated by beam 513a, 513b). The second lens 515 focuses this light 517 towards an input end of an optical fiber 519 positioned at or near the focal point 521 of the second lens 515.

However, light from the source 501 (i.e., in collimated beam 509a, 509b) that is of wavelengths in a second spectral band passes through the dichroic mirror 511 and is instead reflected by the second mirror 523 (as indicated by beam 525a, 525b). In some specific implementations, the dichroic mirror 511 is designed to transmit light in at least the blue part of the spectrum. Accordingly, the second mirror 523 is designed to reflect in at least the blue part of the spectrum (although it would typically reflect the entire visible spectrum). Blue light passes through dichroic mirror 511, is reflected by the second mirror 523 along path 525a, 525b, and then passes back through dichroic mirror 511 to join the beam 513a, 513b that was reflected by the dichroic mirror 511.

In the example of FIG. 5A, light ray 525a and light ray 525b are examples of two different beams of blue light that have passed through the dichroic mirror 511 and are then reflected by the second mirror 523 at different locations of the second mirror 523. After being reflected by the second mirror 523, the blue light ray 525b passes back through the dichroic mirror 511 and is directed towards a location on the surface of the second lens 515. However, the other blue light ray 525a is displaced such that it misses the rest of the optical system 500 and is not collected by second lens 515 and focused onto the end of the optical fiber 519. Accordingly, the separation between second mirror 523 and dichroic mirror 511 can cause some or all of the blue light emitted by white LED 501 to not reach optical fiber 519. By controllably adjusting this separation, the optical system 500 can vary the amount of blue light that reaches the optical fiber 519 and that is included in the output light of the optical system 500. In particular, the optical system 500 of FIG. 5 is configured to include a mechanical movement stage for linearly adjusting a position of the second mirror 523 relative to the position of the dichroic mirror 511 along linear axis 527 and to thereby controllably adjust the proportion of blue light that ultimately reaches the optical fiber (14).

Figure 5B:
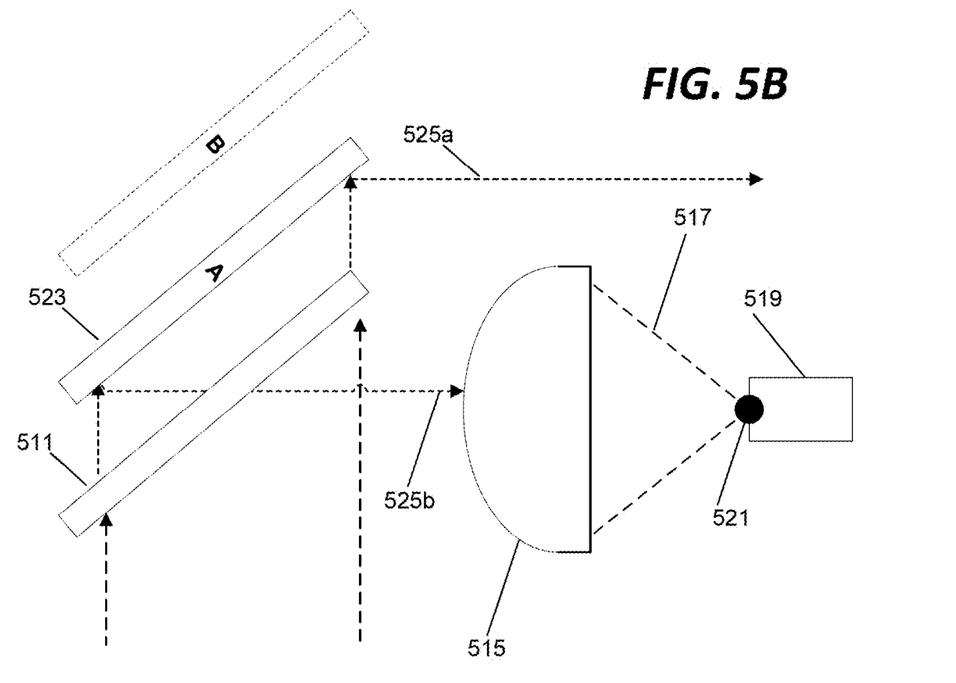
FIG. 5B is a schematic diagram of the illumination system of FIG. 5A with the linearly translatable mirror in a first position.
Figure 5C:
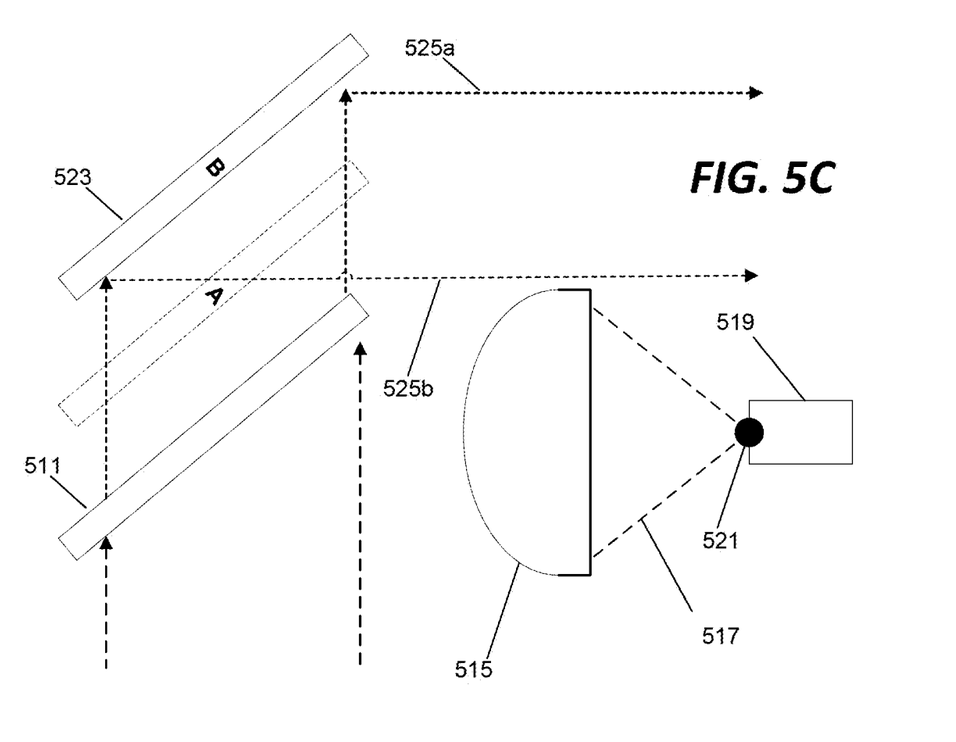
FIG. 5C is a schematic diagram of the illumination system of FIG. 5A with the linearly translatable mirror in a second position.

To further illustrate this control mechanism, FIGS. 5B and 5C illustrate two further examples in which the second mirror 523 is moved to increase the linear distances between the dichroic mirror 511 and the second mirror 523. When the second mirror 523 is in a first position ("Position A" as shown in FIG. 5B), some of the light rays reflected by the second mirror 523 reach the second lens 515 (e.g., blue light ray 525b) while some of the light rays reflected by the second mirror 523 do not reach the second lens 515 (e.g., blue light ray 525a). However, when the second mirror 523 is moved along the linear axis to a second position ("Position B" as shown in FIG. 5C) that is further away from the dichroic mirror 511, both of the illustrated light rays 525a and 525b miss the second lens 515. Accordingly, by moving the second mirror 523 linearly to increase the separation from the dichroic mirror, the amount of blue light that is reflected to the second lens 515 is reduced. In turn, this reduces (or eliminates) the proportion of blue light included in the output light of the optical system 500. Conversely, moving the second mirror 523 linearly towards the dichroic mirror 511 will increase the amount of blue light that is reflected to the second lens 515 and thereby increases the proportion of blue light included in the output light of the optical system 500.

Although the example of FIGS. 5A, 5B, and 5C illustrates adjusting the amount of light in a particular spectral band that is included in the total light output of the optical system by moving the second mirror 523 linearly in a particular direction (i.e., along a linear axis that is generally parallel to the direction in which light approaches the second mirror 523 from the first lens 505), other implementations may be configured to adjust the position of the second mirror in other linear directions or to adjust the position of other components (e.g., the second lens 515) relative to the second mirror 523. Furthermore, although the example of FIGS. 5A, 5B, and 5C uses linear translation of the second mirror 523 while keeping the orientation of the second mirror 523 generally parallel to dichroic mirror 511, rotation of mirror (24) to an orientation not parallel to dichroic mirror (22) can have a similar effect.

FIG. 6 illustrates an example of yet another optical system 600 in which a white LED 601 positioned at or near the focal point 603 of a first lens 605 emits light 607 that is collimated by the first lens and directed towards a dichroic mirror 611 (as illustrated by light beams 609a, 609b). Light of a first spectral band(s) is reflected by the dichroic mirror 611 (as illustrated by light beams 613a, 613b) towards a second lens 615 that focuses the light 617 towards an input end of an optical fiber 619 positioned at or near a focal point 621 of the second lens 615. However, light of a second spectral band is transmitted through the dichroic mirror 611 towards a second mirror 623, which in turn reflects the light of the second spectral band as illustrated by light rays 625a, 625b. The second mirror 623 is mechanically coupled to a rotational stage and, therefore, the direction of the light reflected by the second mirror 623 is controllably adjusted by adjusting a rotational position of the second mirror 623 as described in further detail below.

The light source 601 is not actually a "point source" and is instead an object with finite width. Accordingly, placing this object (i.e., the white LED 601) at the focal plane of first lens 605 will cause a real image of the object to be projected at the focal plane of the second lens 615. With careful alignment, this projected image will overlap onto the end of optical fiber 619. Thus, the intensity of light entering the optical fiber will be similar to what would enter if the end of the fiber 619 were placed into direct contact with light source 601. If this alignment is achieved with a mirror (e.g., dichroic mirror 611), then the first image (i.e., an image including light reflected by the dichroic mirror 611) will fully cover the end of the optical fiber 619, resulting in maximum coupling into the fiber 619. Similarly, the rotational position of the second mirror 623 can be adjusted to align a second image (i.e., an image including light transmitted through the dichroic mirror 611 and reflected by the second mirror 623) with the input end of the optical fiber 619. However, further adjustment of the rotational position of the second mirror will alter the alignment of the second image relative to the end of the optical fiber 619 and thereby adjust a proportion of the second image that enters the optical fiber 619.

Figure 6A:
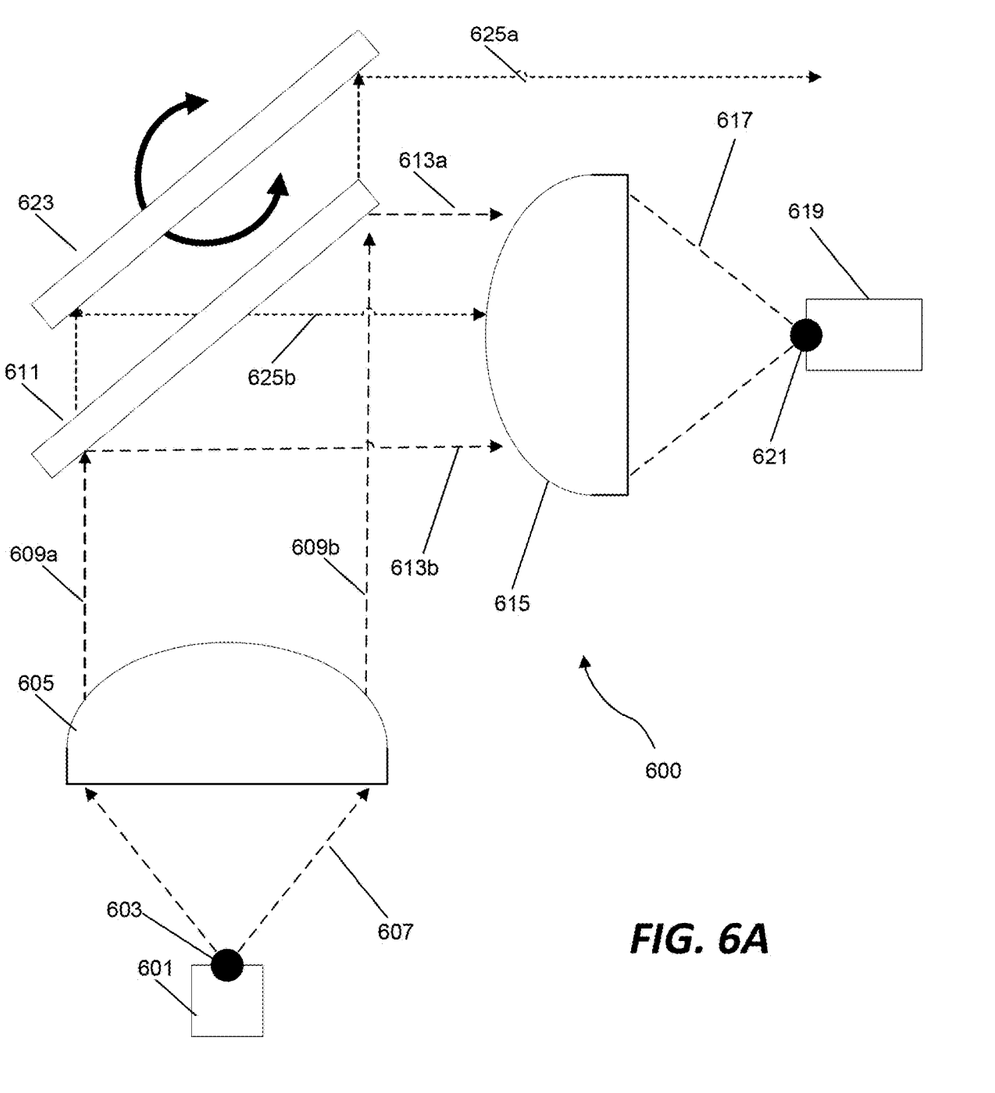
FIG. 6A is a schematic diagram of an illumination system configured to adjust an amount of light of a second spectral band that is projected to an input end of an optical fiber by controllably adjusting a rotational position of a second mirror relative to a dichroic mirror.

The optical system 600 is configured to utilize this alignment effect to controllably regulate a proportion of light from the second spectral band that is included in the light output of the optical system 600 by controllably adjusting the rotational position of the second mirror 623. In the specific example illustrated in FIG. 6A, the dichroic mirror 611 is configured to transmit blue light and to reflect yellow light. The dichroic mirror 611 is positioned to fully align the projected yellow light image with the input end of the optical fiber 619. However, due to the rotational position of the second mirror 623 as illustrated in FIG. 6A, the projected blue light image (i.e., blue light reflected by the second mirror 623) does not fully align with the input end of the optical fiber 619.

Figure 6B:
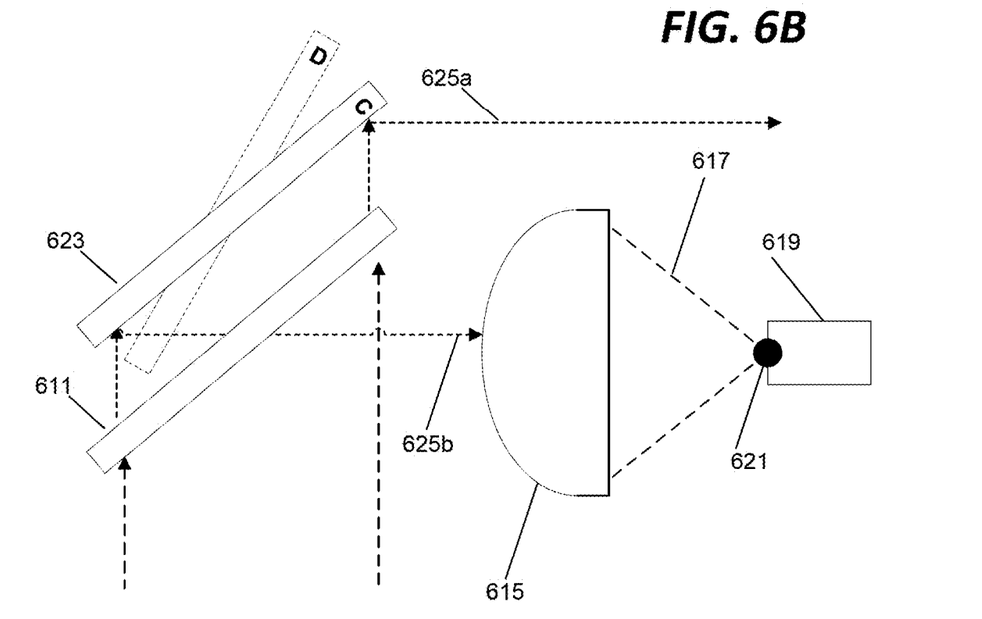
FIG. 6B is a schematic diagram of the illumination system of FIG. 6A with the second mirror in a first rotational position.
Figure 6C:
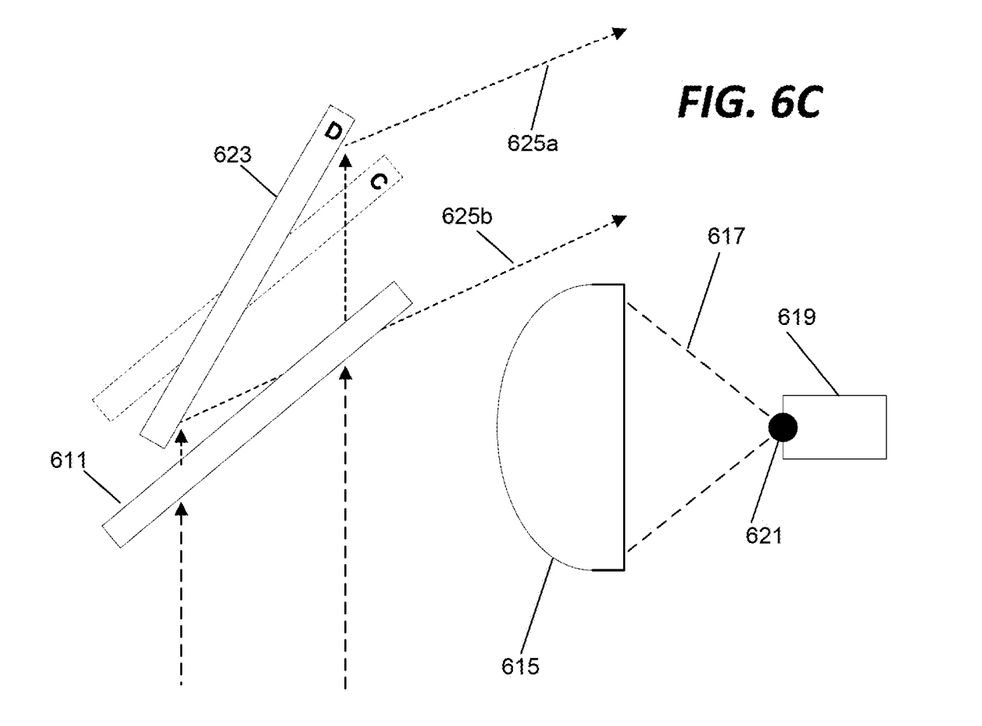
FIG. 6C is a schematic diagram of the illumination system of FIG. 6A with the second mirror in a second rotational position.

FIGS. 6B and 6C show the optical system 600 with the second mirror 623 moving from a first rotational position ("Position C") to a second rotational position ("Position D"). When in the first rotational position ("Position C" as shown in FIG. 6B), some of the light rays (e.g., light ray 625b) reflected by the second mirror 623 reach the second lens 615 and are, therefore, included in the focused light 617 delivered to the optical fiber 619 while other light rays (e.g., light ray 625a) miss the second lens 615 and, therefore, are not included in the focused light 617 delivered to the optical fiber 619. However, when the rotational angle of the second mirror 623 is adjusted, the angle at which the light is reflected is changes and, as shown in the example of FIG. 6C, light rays (e.g., light ray 525b) that were directed towards the second lens 615 in the first rotational position ("Position C") no longer reach the second lens 615 in the second rotational position ("Position D"). Accordingly, by changing the rotational position of the second mirror 623 from Position C to Position D, the portion of light of the second spectral band (e.g., blue light) that is included in the light output of the optical system 600 is controllably decreased. Conversely, rotating the second mirror 623 in the opposite direction would better align the projected light rays with the second lens 615 and would increase the portion of light of the second spectral band (e.g., blue light) that is included in the light output of the optical system 600.

Figure 7:
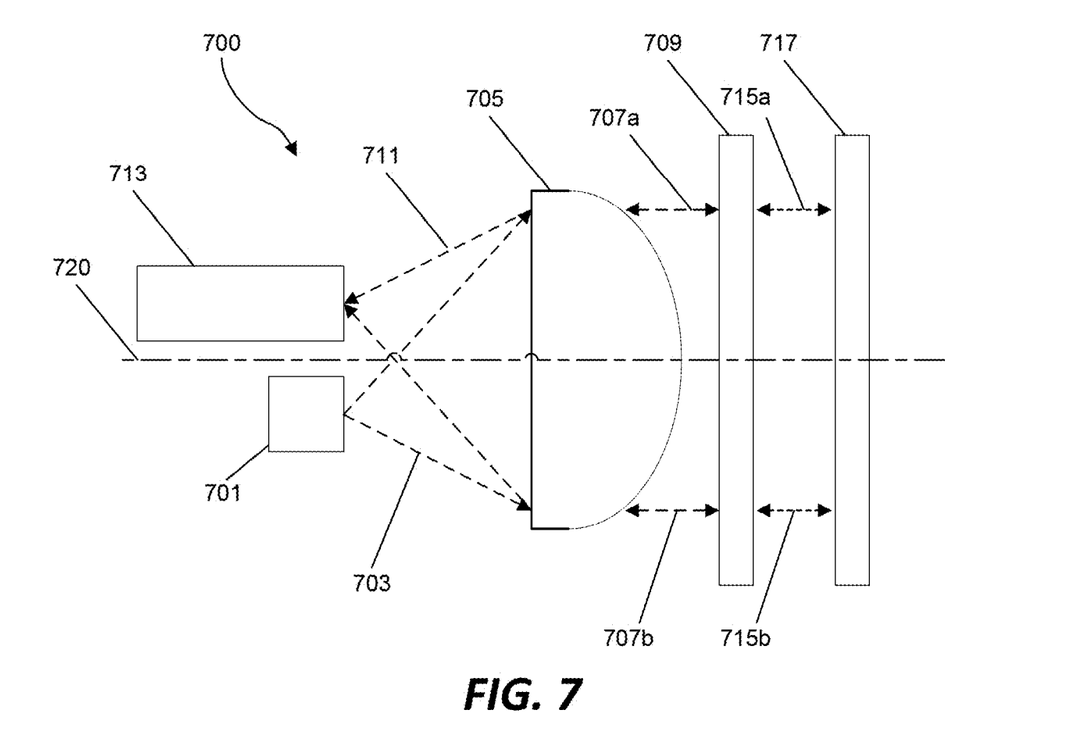
FIG. 7 is a schematic diagram of an illumination system with a dichroic mirror and a second mirror configured to selectively reflect light of a particular wavelength (or bandwidth of wavelengths) along an optical path that is angled at nearly 180 degrees from a light source to an input end of an optical fiber.

In the examples described above, the optical systems each include two lenses. However, the mechanisms for controllably adjusting a proportion of light from a particular spectral band (e.g., blue light) that is provided to an optical fiber can also be implemented in systems that include only a single lens. FIG. 7 shows one example of an optical system 700 with only one lens 705. In the optical system 700, a light source 701 emits light 703 towards the lens 705. The lens 705 collimates the light and directs the collimates light beam (illustrated by light rays 707a and 707b) toward a dichroic mirror 709. Light of a first spectral band(s) is reflected by the dichroic mirror 709 while light of a second spectral band is transmitted through the dichroic mirror 709 towards a second mirror 717 (as illustrated by light rays 715a, 715b). In some of the examples described above, the mirrors turned the collimated beam from the first lens through an angle of approximately 90° to reach a second lens and be focused to an image projected onto the end of the optical fiber. However, in the optical system 700 of FIG. 7, the dichroic mirror 709 is positioned to turn the collimated beam (e.g., light rays 707a, 707b) through an angle of approximately 180° to pass back through the first lens 705. If the angle were exactly 180°, the position of the projected image would coincide with the location of the light source 701. However, in the example of FIG. 7, the light source 701 is offset to one side of the optic axis 720 through the lens 705 and mirrors 709, 717. This results in the projected image (i.e., the light 711 focused by the lens 705) being displaced to the opposite side of the optic axis 720, where it can be brought into coincidence with the end of an optical fiber 713.

As with the two lens arrangements, there are two projected images in the optical system of FIG. 7. A first image is formed by light reflected by the dichroic mirror 709 (e.g., a yellow light image) and is projected toward the distal end of the optical fiber 713. A second image is formed by light passing through the dichroic mirror 709 and reflected by the second mirror 717 (e.g., a blue light image). Accordingly, the portion of light of the second spectral band (e.g., blue light) that is projected to the input end of the optical fiber 713 and included in the light output of the optical system 700 can be modulated by adjusting the position of the second mirror 717. For example, linear translation of the second mirror 717 to increase the distance between the second mirror 717 and the dichroic mirror 709 will result in losses which reduce the intensity of the blue image that is projected at the end of the optical fiber 713. Alternatively, rotation of second mirror 717 can also be used to controllably adjust a displacement of blue image relative to yellow image. If the system 700 has been aligned so that the yellow image fully overlaps the end of optical fiber 713, then the proportion of blue light, relative to yellow light, which enters the optical fiber 713 can be modulated by mechanical rotation of second mirror 717.

In some implementations, the mechanism for controlling a linear position or rotational position of the second mirror (e.g., second mirror 523, 623, 717) can be implemented as a manual control on an exterior of the optical system that is mechanically coupled to the second mirror. For example, a linear slider knob mechanically coupled to a mounting bracket carrying the second mirror 523 can be used to controllably adjust the proportion of blue light in the example of FIG. 5A. Similarly, a rotating knob coupled to a mounting bracket carrying the second mirror 623 can be used to controllably adjust the proportion of blue light in the example of FIG. 6.

Figure 8:
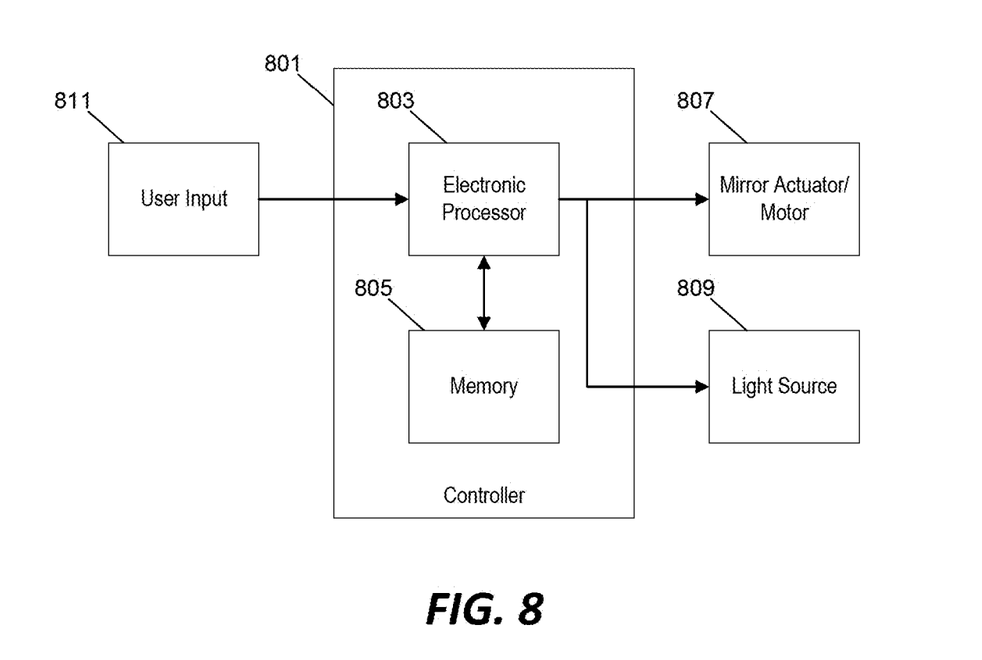
FIG. 8 is a block diagram of a control system for operating the illumination system of FIGS. 5A through 7 according to one embodiment.

However, in other implementations, the movement of the second mirror and, in turn, the proportion of blue light that is emitted by the device can be regulated by an electronic controller. FIG. 8 illustrates a block diagram of a control system that can be used to regulate the amount of blue light that is emitted by the optical system. A controller 801 includes an electronic processor 803 and a computer-readable non-transitory memory 805. The memory 805 stores instructions that are accessed and executed by the electronic processor 803 to provide certain functionality of the optical system. In the example of FIG. 8, the electronic processor 803 is coupled to a light source 809 to controllably activate, deactivate, or modulate the intensity of the light source (e.g., the white LED discussed in the examples above). The electronic processor 803 is also communicatively coupled to a mirror actuator 807 that is configured to controllably adjust a linear and/or rotational position of the second mirror in the examples described above. In some implementations, the mirror actuator 807 includes a motor that is either directly or indirectly coupled to a bracket carrying the second mirror. Accordingly, operation of the motor 807 causes a rotation and/or a linear movement of the second mirror in order to controllably adjust the proportion of blue light that is projected to the end of the optical fiber and ultimately emitted by the optical system.

If incorporated into a fiberoptic illumination system for ophthalmic surgery, an optical system utilizing an arrangement such as illustrated in the examples of FIG. 5A, 6A, or 7 allows the surgeon to vary the proportion of blue light that is emitted by the optical system, so as to reduce phototoxicity but still be able to select white light when needed for optimum visualization.

Although some of the examples described above specifically describe mechanisms for controllably adjusting a proportion of blue light in an output of an optical systems, the systems and methods described above may be adapted in some implementations to controllably adjust a proportion of a different spectral band of light in the light output of the system. Furthermore, although the examples above discuss adjusting a position of the second mirror in order to adjust the proportion of certain spectral bands of light in the final light output, other implementations may be configured to controllably adjust the proportion by adjusting the position of other components. For example, an optical system may be adapted to provide controllable linear and/or rotational movement of a dichroic mirror and some such implementations may be configured to adjust the proportion of light of a particular spectral band that is included in the final light output of the optical system by controllably adjusting the amount of light reflected by the dichroic mirror that reaches the input end of the optical fiber while the position of the second mirror remains fixed and fully aligned with the input end of the optical fiber. In still other implementations, the positions of both the dichroic mirror and the second mirror may be controllably adjusted independently to more specifically tune the spectral composition of the light output of the optical system. Finally, some implementations may include multiple different dichroic mirrors positioned to further separate the light beam into different spectral bands.

Thus, the invention provides, among other things, a system and method for controllably adjusting a proportion of light of a particular wavelength (or bandwidth of wavelengths) that is included in the light emitted by an optical system. Various features and advantages of the invention are set forth in the following claims.

What is claimed is:

1. An optical system comprising:
   a light source;
   a dichroic mirror configured to reflect light of a first spectral band from the light source towards a distal end of an optical fiber while allowing light of a second spectral band to pass through the dichroic mirror;
   a second mirror positioned behind the dichroic mirror and configured to reflect light of the second spectral band; and
   a mirror actuator coupled to the second mirror and configured to adjust a proportion of the light of the second spectral band that is emitted by the optical system by adjusting a position of the second mirror relative to the dichroic mirror, wherein adjusting the position of the second mirror relative to the dichroic mirror alters the amount of the light of the second spectral band reflected by the second mirror that reaches the distal end of the optical fiber.

2. The optical system of claim 1, wherein the second mirror is positioned so that a surface of the second mirror is parallel to a surface of the dichroic mirror, and wherein the mirror actuator is configured to controllably adjust a distance between the second mirror and the dichroic mirror by linearly adjusting a position of the second mirror.

3. The optical system of claim 1, wherein the mirror actuator is configured to controllably adjust a rotational angle of the second mirror relative to the dichroic mirror.

4. The optical system of claim 1, further comprising
   a first lens positioned on an optical path between the light source and the dichroic mirror, wherein the first lens is configured to collimate light from the first light source; and
   a second lens positioned on an optical path between the dichroic mirror and the distal end of the optical fiber, wherein the second lens is configured to focus collimator light from the dichroic mirror to a focal plane aligned with the distal end of the optical fiber.

5. The optical system of claim 4, wherein the dichroic mirror is positioned to reflect light from the first lens approximately 90 degrees towards the second lens.

6. The optical system of claim 1, further comprising a lens positioned between the light source and the dichroic mirror,
   wherein the light source is positioned at an offset from an optical axis of the lens, and
   wherein the distal end of the optical fiber is positioned at a corresponding offset from the optical axis of the lens so that light from the light source is collimated by the lens before reaching the dichroic mirror and light reflected by the dichroic mirror is focused by the lens to a focal plane aligned with the distal end of the optical fiber.

* * * * *